United States Patent
Kuo

(10) Patent No.: US 11,571,156 B2
(45) Date of Patent: Feb. 7, 2023

(54) RENAL FUNCTION ASSESSMENT METHOD, RENAL FUNCTION ASSESSMENT SYSTEM AND KIDNEY CARE DEVICE

(71) Applicant: China Medical University, Taichung (TW)

(72) Inventor: Chin-Chi Kuo, Taichung (TW)

(73) Assignee: China Medical University, Taichung (TW)

( * ) Notice: Subject to any disclaimer, the term of this patent is extended or adjusted under 35 U.S.C. 154(b) by 346 days.

(21) Appl. No.: 16/855,019

(22) Filed: Apr. 22, 2020

(65) Prior Publication Data

US 2021/0244327 A1   Aug. 12, 2021

(30) Foreign Application Priority Data

Feb. 10, 2020 (TW) ................................ 109104101

(51) Int. Cl.
*A61B 5/20* (2006.01)
*G06T 7/00* (2017.01)
(Continued)

(52) U.S. Cl.
CPC ............ *A61B 5/201* (2013.01); *G06K 9/6256* (2013.01); *G06K 9/6267* (2013.01);
(Continued)

(58) Field of Classification Search
CPC .... A61B 5/201; G06K 9/6256; G06K 9/6267; G06T 7/0012; G06T 2207/10132;
(Continued)

(56) References Cited

U.S. PATENT DOCUMENTS 9,198,635 B2    12/2015  Crum et al.
2009/0203997 A1*  8/2009  Ustuner .............. G01S 7/52071
                                                                600/443
(Continued)

FOREIGN PATENT DOCUMENTS

| TW | 201800057 A | 1/2018 | |
| TW | 202004774 | * 1/2020 | ............. A61B 8/085 |
| TW | 202004774 A | 1/2020 | |

OTHER PUBLICATIONS

Kuo et al, ("Automation of the kidney function prediction and classification through ultrasound-based kidney imaging using deep learning", Apr. 26, 2019, npi Digital Medicine (2019), pp. 1-9) (Year: 2019).*

(Continued)

*Primary Examiner* — Amara Abdi
(74) *Attorney, Agent, or Firm* — Servilla Whitney LLC

(57) ABSTRACT

A renal function assessment method includes following steps. A target kidney ultrasound image data of a subject is provided. An image pre-processing step is performed, wherein an image size of the target kidney ultrasound image data is adjusted, and the target kidney ultrasound image data is normalized according to an average and a standard deviation of a visual image database to obtain an after-processed target kidney ultrasound image data. A feature extracting step is performed, wherein the after-processed target kidney ultrasound image data is trained to achieve a convergence by a first deep-learning classifier to obtain an image feature of the after-processed target kidney ultrasound image data. A determining step is performed, wherein the image feature of the after-processed target kidney ultrasound image data is analyzed by the first deep-learning classifier to obtain an assessing result of an estimated glomerular filtration rate (eGFR).

18 Claims, 13 Drawing Sheets

(51) Int. Cl.
*G06K 9/62* (2022.01)
*G06V 10/40* (2022.01)

(52) U.S. Cl.
CPC ............ *G06T 7/0012* (2013.01); *G06V 10/40* (2022.01); *G06T 2207/10132* (2013.01); *G06T 2207/20081* (2013.01); *G06T 2207/30084* (2013.01)

(58) Field of Classification Search
CPC . G06T 2207/20081; G06T 2207/30084; G06T 2207/20084; G06V 10/40; G06V 10/454; G06V 10/82; G06V 2201/03
See application file for complete search history.

(56) References Cited

U.S. PATENT DOCUMENTS

| | | | |
|---|---|---|---|
| 2010/0249598 A1 | 9/2010 | Smith et al. | |
| 2011/0137170 A1* | 6/2011 | Yang | G06T 7/0012 |
| | | | 600/443 |
| 2014/0148689 A1* | 5/2014 | Lee | A61B 8/467 |
| | | | 600/424 |

OTHER PUBLICATIONS

Kuo, Chin-Chi, et al., "Automation of the kidney function prediction and classification through ultrasound-based kidney imaging using deep learning", Apr. 26, 2019, 1-9.

* cited by examiner

RENAL FUNCTION ASSESSMENT METHOD, RENAL FUNCTION ASSESSMENT SYSTEM AND KIDNEY CARE DEVICE

RELATED APPLICATIONS

This application claims priority to Taiwan Application Serial Number 109104101, filed Feb. 10, 2020, which is herein incorporated by reference.

BACKGROUND

Technical Field

The present disclosure relates to a medical information analysis system, a method and a device thereof. More particularly, the present disclosure relates to a renal function assessment method, a renal function assessment system and a kidney care device.

Description of Related Art

Among many chronic diseases, the incidence and the prevalence of chronic kidney disease (CKD) in Taiwan are ranked first all over the world. Therefore, how to detect the damage of kidney timely and early to prevent the incidence of the CKD is very important.

Estimated Glomerular filtration rate ("eGFR" hereafter) is a biomarker of early kidney injury screening and can facilitate the diagnosis of chronic kidney disease, wherein eGFR is estimated using Modification of Diet in Renal Disease (MDRD) study equation (eGFR=186×(Serum creatinine level)$^{-1.154}$× (age)$^{-0.203}$×1.212×0.742 [if female]) based on the serum creatinine level and the age, the gender and the race of the subject. The course of CKD can be divided into five stages base on the value of eGFR to assess the renal function of the subject. However, the estimation of eGFR should be based on serum creatinine level, so that it is unavoidable to take a blood sample of the subject in an invasive manner to test the level of serum creatinine therein.

Along with the advance of the imaging technology, non-invasive imaging methods are applied to assess the renal function of patients, wherein the kidney ultrasound images can be used to assess whether the kidney of the patient is suffered from the symptoms such as atrophy of kidney, kidney stones, kidney tumors, polycystic kidney disease, renal medulla calcification or edema or not. However, the kidney ultrasound images must be interpreted by a nephrologist, the interpretation results of renal ultrasound images of the same subject are likely to vary due to subjective interpretation habits of different nephrologists. Thus, the accuracy of the assessment of the renal function based on clinicians' interpretation of kidney ultrasound images is operator dependent and not consistent across different clinicians.

Therefore, how to develop a rapid, low-cost and highly accurate assessing method of the renal function is a technical issue with clinical application value.

SUMMARY

According to one aspect of the present disclosure, a renal function assessment method includes following steps. A target kidney ultrasound image data of a subject is provided. An image pre-processing step is performed, wherein an image size of the target kidney ultrasound image data is adjusted, and the target kidney ultrasound image data is normalized according to an average and a standard deviation of a visual image database to obtain an after-processed target kidney ultrasound image data. A feature extracting step is performed, wherein the after-processed target kidney ultrasound image data is trained to achieve a convergence by a first deep-learning classifier to obtain an image feature of the after-processed target kidney ultrasound image data. A determining step is performed, wherein the image feature of the after-processed target kidney ultrasound image data is analyzed by the first deep-learning classifier to obtain an assessing result of an estimated glomerular filtration rate (eGFR).

According to another aspect of the present disclosure, a renal function assessment system includes an image capturing device and a processer. The image capturing device is for capturing a target kidney ultrasound image data of a subject. The processer is electronically connected to the image capturing device, wherein the processer includes a reference kidney ultrasound image database and a renal function assessment program, and the reference kidney ultrasound database includes a plurality of reference kidney ultrasound image data. The renal function assessment program includes an image sampling model, a reference image pre-processing model, a training model, a target image pre-processing model and a comparing model. The image sampling model is for sampling the reference kidney ultrasound image data randomly by an ensemble learning module to obtain a testing image dataset and a validation image dataset. The reference image pre-processing model is for adjusting an image size of each of the reference kidney ultrasound image data of the testing image dataset, wherein each of the reference kidney ultrasound image data is normalized according to an average and a standard deviation of a visual image database to obtain a plurality of after-processed reference kidney ultrasound image data. The training model is for achieving a convergence of the after-processed reference kidney ultrasound image data by a deep learning module to obtain a first deep-learning classifier. The target image pre-processing model is for adjusting an image size of the target kidney ultrasound image data, wherein the target kidney ultrasound image data is normalized according to the average and the standard deviation of the visual image database to obtain an after-processed reference kidney ultrasound image data. The comparing model is for achieving a convergence of the after-processed target kidney ultrasound image data by the first deep-learning classifier to obtain an image feature of the after-processed target kidney ultrasound image data, wherein the image feature of the after-processed target kidney ultrasound image data is analyzed by the first deep-learning classifier o obtain an assessing result of an estimated glomerular filtration rate (eGFR).

According to further another aspect of the present disclosure, a kidney care device includes the renal function assessment system according to the aforementioned aspect and an electronic device, and the electronic device is electronically connected to the renal function assessment system.

BRIEF DESCRIPTION OF THE DRAWINGS

The present disclosure can be more fully understood by reading the following detailed description of the embodiment, with reference made to the accompanying drawings as follows.

DETAILED DESCRIPTION

The present disclosure will be further exemplified by the following specific embodiments to facilitate utilizing and practicing the present disclosure completely by the people skilled in the art without over-interpreting and over-experimenting. However, these practical details are used to describe how to implement the materials and methods of the present disclosure and are not necessary.

The Renal Function Assessment Method of the Present Disclosure

Figure 1:
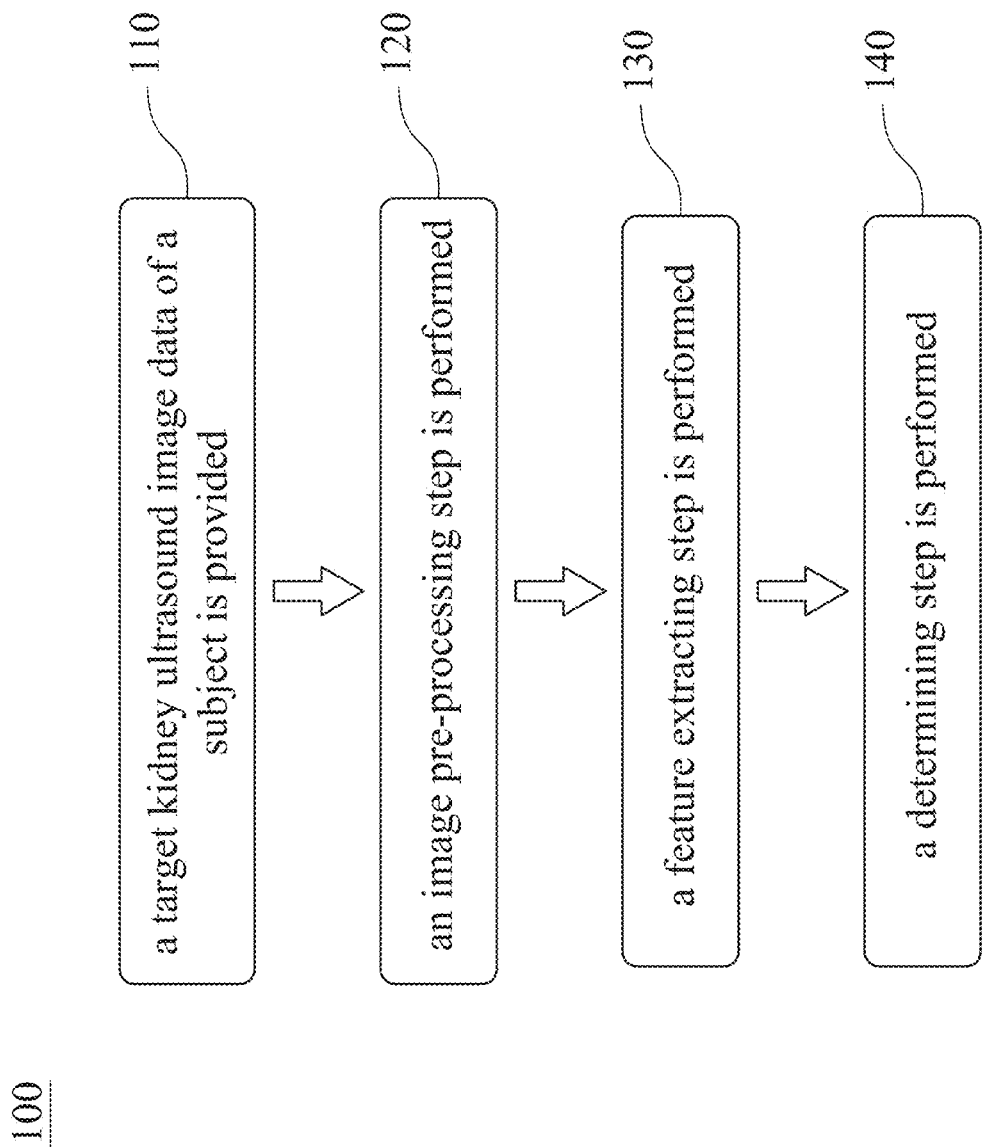
FIG. 1 is a flow chart of a renal function assessment method according to one embodiment of the present disclosure.

Please refer to FIG. 1, which is a flow chart of a renal function assessment method 100 according to one embodiment of the present disclosure. The renal function assessment method 100 includes Step 110, Step 120, Step 130 and Step 140.

In Step 110, a target kidney ultrasound image data of a subject is provided. In detail, the target kidney ultrasound image data can be connected to an electronic medical record (EMR) of the subject, and the EMR can include the information of the gender and the age of the subject, the laboratory test results (such as serum creatinine) or other special treatment procedures, such as medication history, comorbidities, or admission records, so that it is favorable for facilitating the following assessment and comparison.

In Step 120, an image pre-processing step is performed, wherein an image size of the target kidney ultrasound image data is adjusted, and the target kidney ultrasound image data is normalized according to an average and a standard deviation of a visual image database to obtain an after-processed target kidney ultrasound image data. In detail, the image size of the target kidney ultrasound image data will be adjusted to 224 pixels×224 pixels based on an area where the kidney is located, and the target kidney ultrasound image data will be normalized according to an average and a standard deviation of Neo4j visual image database, ImageNet visual image database or CIFAR-10 visual image database to facilitate the following analysis, but the present disclosure is not limited thereto.

Furthermore, in Step 120, the target kidney ultrasound image data can be further processed by an image data reinforcement method. In detail, the target kidney ultrasound image data is processed by a displacement noise reinforcing method, a rolling noise reinforcing method or a horizontal flip noise reinforcing method in the image data reinforcement method to increase the amount of information of the target kidney ultrasound image data, so that it is favorable for enhancing the accuracy of the following assessment.

In Step 130, a feature extracting step is performed, wherein the after-processed target kidney ultrasound image data is trained to achieve a convergence by a first deep-learning classifier to obtain an image feature of the after-processed target kidney ultrasound image data. In detail, the renal function assessment method 100 of the present disclosure can analyze the image information of the after-processed target kidney ultrasound image data and then extract a corresponding image feature automatically by the first deep-learning classifier, so that the assessing efficiency of the renal function assessment method 100 of the present disclosure can be enhanced.

In Step 140, a determining step is performed, wherein the image feature of the after-processed target kidney ultrasound image data is analyzed by the first deep-learning classifier to obtain an assessing result of an estimated glomerular filtration rate ("eGFR" hereafter).

Figure 2:
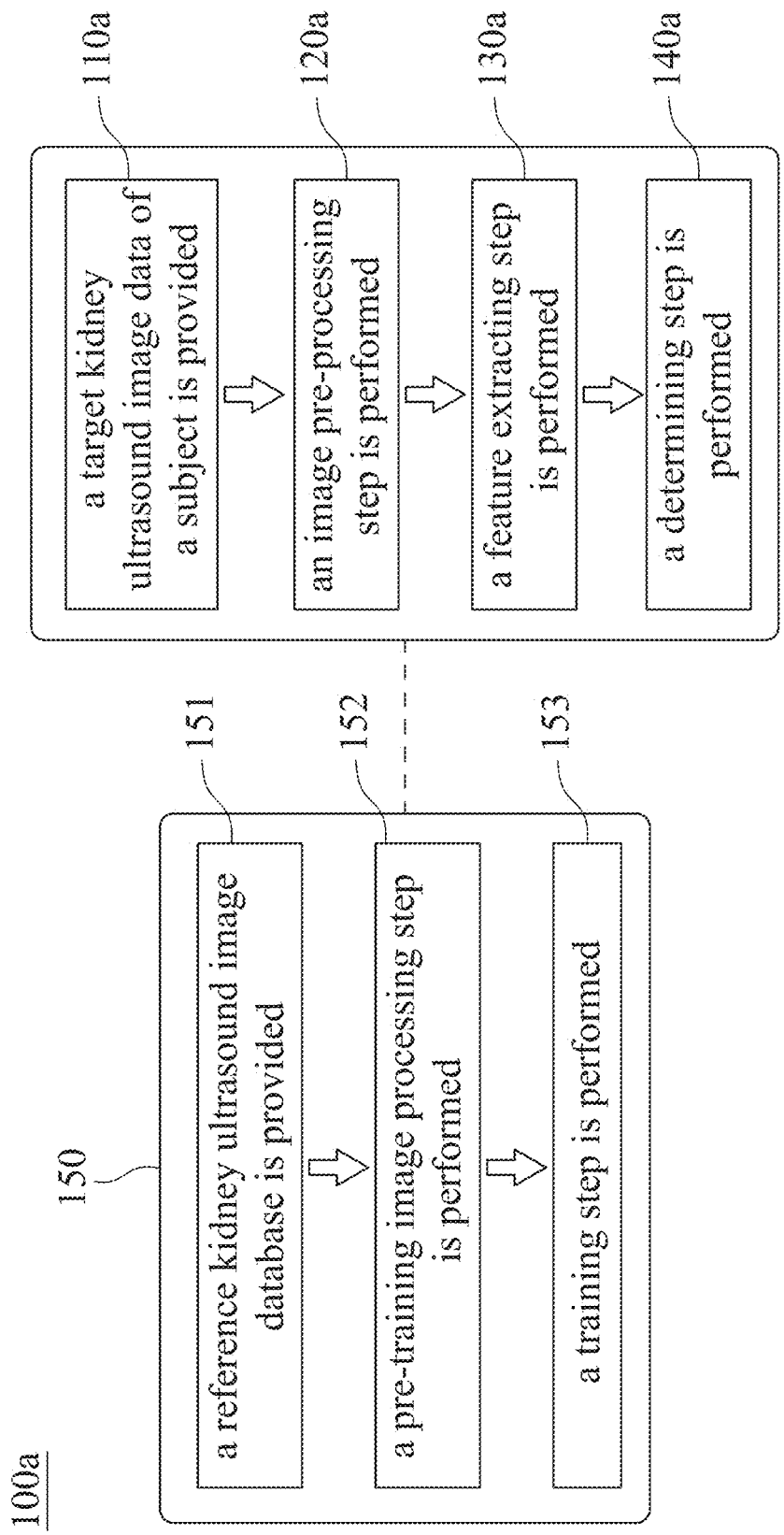
FIG. 2 is a flow chart of a renal function assessment method according to another embodiment of the present disclosure.

Furthermore, please refer to FIG. 1 and FIG. 2 simultaneously, wherein FIG. 2 is a flow chart of a renal function assessment method 100a according to another embodiment of the present disclosure. The renal function assessment method 100a includes Step 110a, Step 120a, Step 130a, Step 140a and Step 150, wherein Step 110a, Step 120a, Step 130a and Step 140a are the same with Step 110, Step 120, Step 130 and Step 140 of FIG. 1, so that the details of Step 110a, Step 120a, Step 130a and Step 140a will not be described again therein. The established details of the first deep-learning classifier of the present disclosure will be illustrated by FIG. 1 and FIG. 2. In Step 150, a module establishing step is performed, wherein the module establishing step includes Step 151, Step 152 and Step 153.

In Step 151, a reference kidney ultrasound image database is provided, wherein the reference kidney ultrasound image database includes a plurality of reference kidney ultrasound image data. In detail, each of the reference kidney ultrasound image data can be connected to an EMR of the corresponding reference subject, and the EMR can include the information of the gender and the age of the reference subject, the laboratory test results (such as serum creatinine) or other special treatment procedures, such as medication history, comorbidities, or admission records, to enhance the data integrity of each of the reference kidney ultrasound image data.

In Step 152, a pre-training image processing step is performed, wherein an image size of each of the reference kidney ultrasound image data is adjusted, and each of the reference kidney ultrasound image data is normalized according to the average and the standard deviation of the visual image database as the foregoing described to obtain a plurality of after-processed reference kidney ultrasound image data. In detail, the image size of each of the reference kidney ultrasound image data will be adjusted to 224 pixels× 224 pixels based on an area where the kidney is located, and each of the reference kidney ultrasound image data will be normalized according to the average and the standard deviation of one of Neo4j visual image database, ImageNet visual image database or CIFAR-10 visual image database to facilitate the following analysis. It must be noted that the visual image database in the pre-training image processing step must be the same with that in Step 120 to ensure the consistency and correctness of the renal function assessment method 100 and the renal function assessment method 100a of the present disclosure.

Furthermore, in Step 152, each of the reference kidney ultrasound image data can be further processed by a reference image data reinforcement method in the pre-training image processing step. In detail, each of the reference kidney ultrasound image data is processed by a displacement noise reinforcing method, a rolling noise reinforcing method or a horizontal flip noise reinforcing method in the reference image data reinforcement method to increase the amount of information of each of the reference kidney ultrasound image data. Thus, it is favorable for enhancing the accuracy of the following assessment.

In Step 153, a training step is performed, wherein the training step is for achieving a convergence of the after-processed reference kidney ultrasound image data by a deep learning module to obtain the first deep-learning classifier.

Therefore, in the renal function assessment method 100 and the renal function assessment method 100a of the present disclosure, the target kidney ultrasound image data is processed by the image pre-processing step and then trained by the first deep-learning classifier to achieve a convergence, and the image feature obtained therefrom is further analyzed to assess the renal function of a subject. Accordingly, it can not only provide a rapid, accurate and non-invasive examination method for the renal function evaluation based on the kidney ultrasound image data, but also avoid the assessing error in the conventional renal function assessment method caused by different subjective interpretation habits of different analysts.

Figure 3:
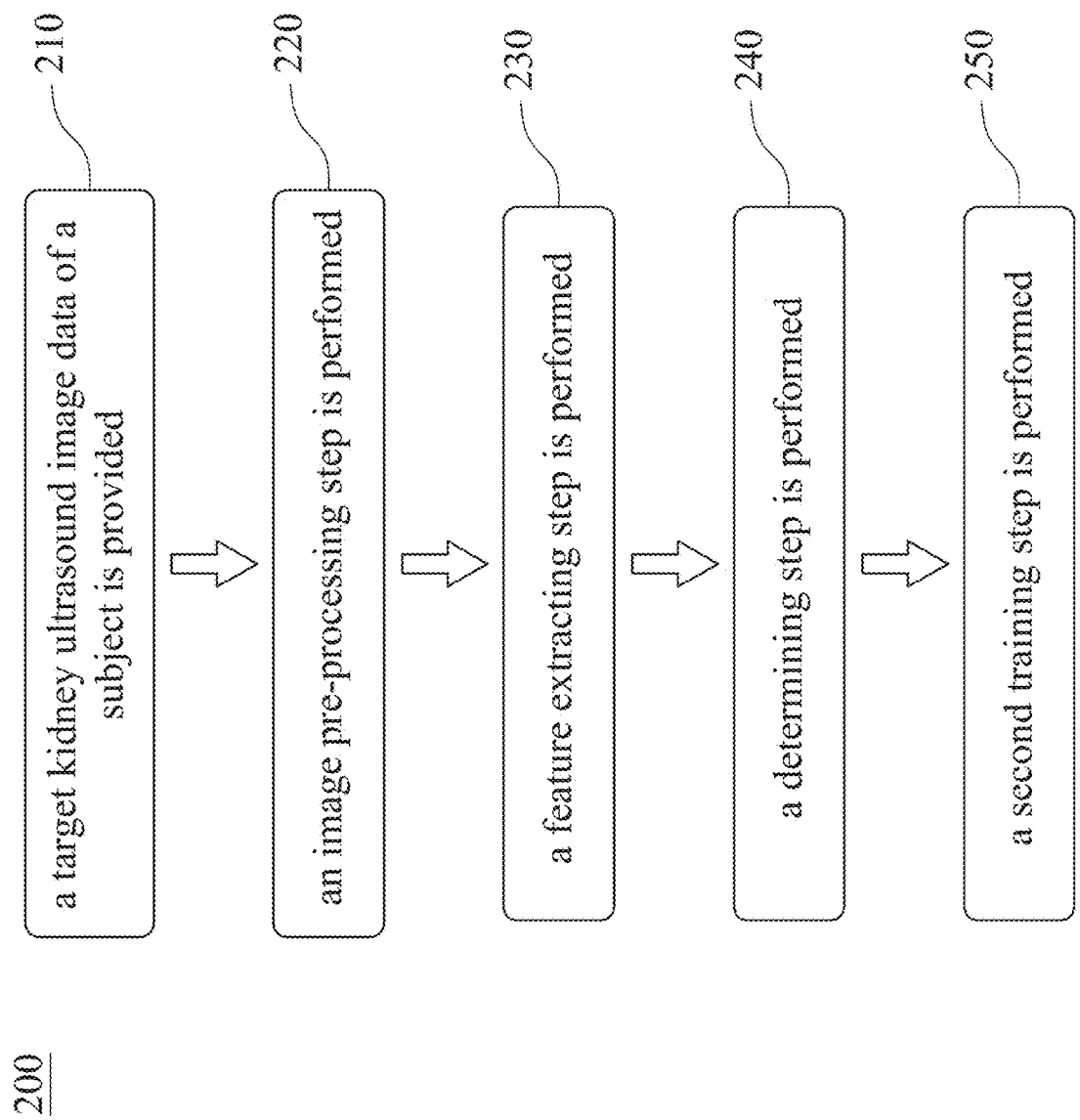
FIG. 3 is a flow chart of a renal function assessment method according to further another embodiment of the present disclosure.

Please refer to FIG. 3, which is a flow chart of a renal function assessment method 200 according to further another embodiment of the present disclosure. The renal function assessment method 200 is similar with the renal function assessment method 100 of FIG. 1 in the details of steps, so that the same details of steps are not described again therein. The renal function assessment method 200 includes Step 210, Step 220, Step 230, Step 240 and Step 250.

In Step 210, a target kidney ultrasound image data of a subject is provided.

In Step 220, an image pre-processing step is performed, wherein an image size of the target kidney ultrasound image data is adjusted, and the target kidney ultrasound image data is normalized according to an average and a standard deviation of a visual image database to obtain an after-processed target kidney ultrasound image data.

In Step 230, a feature extracting step is performed, wherein the after-processed target kidney ultrasound image data is trained to achieve a convergence by a first deep-learning classifier to obtain an image feature of the after-processed target kidney ultrasound image data. The establishing details of the first deep-learning classifier are the same with that described in Step 150, so that the same details will not be described again therein.

In Step 240, a determining step is performed, wherein the image feature of the after-processed target kidney ultrasound image data is analyzed by the first deep-learning classifier to obtain an assessing result of eGFR.

In Step 250, a second training step is performed, wherein a duplicate copy of the image feature of the after-processed target kidney ultrasound image data is trained by a second deep-learning classifier to achieve a convergence and then obtain a second image selected feature weight data, and an assessing status of an advanced chronic kidney disease (CKD) is obtained according to the second image selected feature weight data. The assessing status of the advanced CKD indicates an irreversible kidney failure. In detail, the image feature output from a second fully connected layer of the first deep-learning classifier of the present disclosure has included the eGFR information implied in the target kidney ultrasound image data. In this time, the duplicate copy of the image feature of the after-processed target kidney ultrasound image data will be trained by the second deep-learning classifier to achieve a convergence and then obtain the second image selected feature weight data. In specific, the second deep-learning classifier can be XGBoost classifier (eXtreme Gradient Boosting classifier), but the present disclosure is not limited thereto.

Furthermore, CKD can be divided into five stages (namely Stage 1, Stage 2, Stage 3, Stage 4 and Stage 5) based on the value of eGFR in clinical terms, and the symptoms and the range of the value of eGFR are shown in Table 1.

TABLE 1

| | Symptom | eGFR (ml/min/1.73 m$^2$) |
|---|---|---|
| Stage 1 | Kidney damage (proteinuria or hematuria) with normal kidney function | 90~100 |
| Stage 2 | Mild loss of kidney function with proteinuria or hematuria | 60~89 |
| Stage 3 | 3a: Mild to moderate loss of kidney function 3b: Moderate to severe loss of kidney function | 30~59 |
| Stage 4 | Severe loss of kidney function | 15~29 |
| Stage 5 | Kidney failure and need for transplant or dialysis | <15 |

As shown in Table 1, CKD becomes irreversible after entering into Stage 3, and in this time, the patient must cooperate with the doctor actively to delay the progression of CKD into end-stage renal disease (ESRD). Furthermore, because the critical point of eGFR is 60 ml/min/1.73 m$^2$, the basis of eGFR for determining the second image selected feature weight data of the renal function assessment method 200 of the present disclosure is set as 60 ml/min/1.73 m$^2$ to output the prediction of advanced CKD status under the premise that the current clinical diagnosis standards are satisfied.

Therefore, by the cooperative training and assessment of the first deep-learning classifier and the second deep-learning classifier, the renal function assessment method 200 of the present disclosure can not only assess the value of eGFR of the subject rapidly and accurately according to the target kidney ultrasound image data thereof, but also further determine whether the subject has advanced CKD or not, so that it is favorable for formulating a medical strategy thereof.

The Renal Function Assessment System of the Present Disclosure

Figure 4:
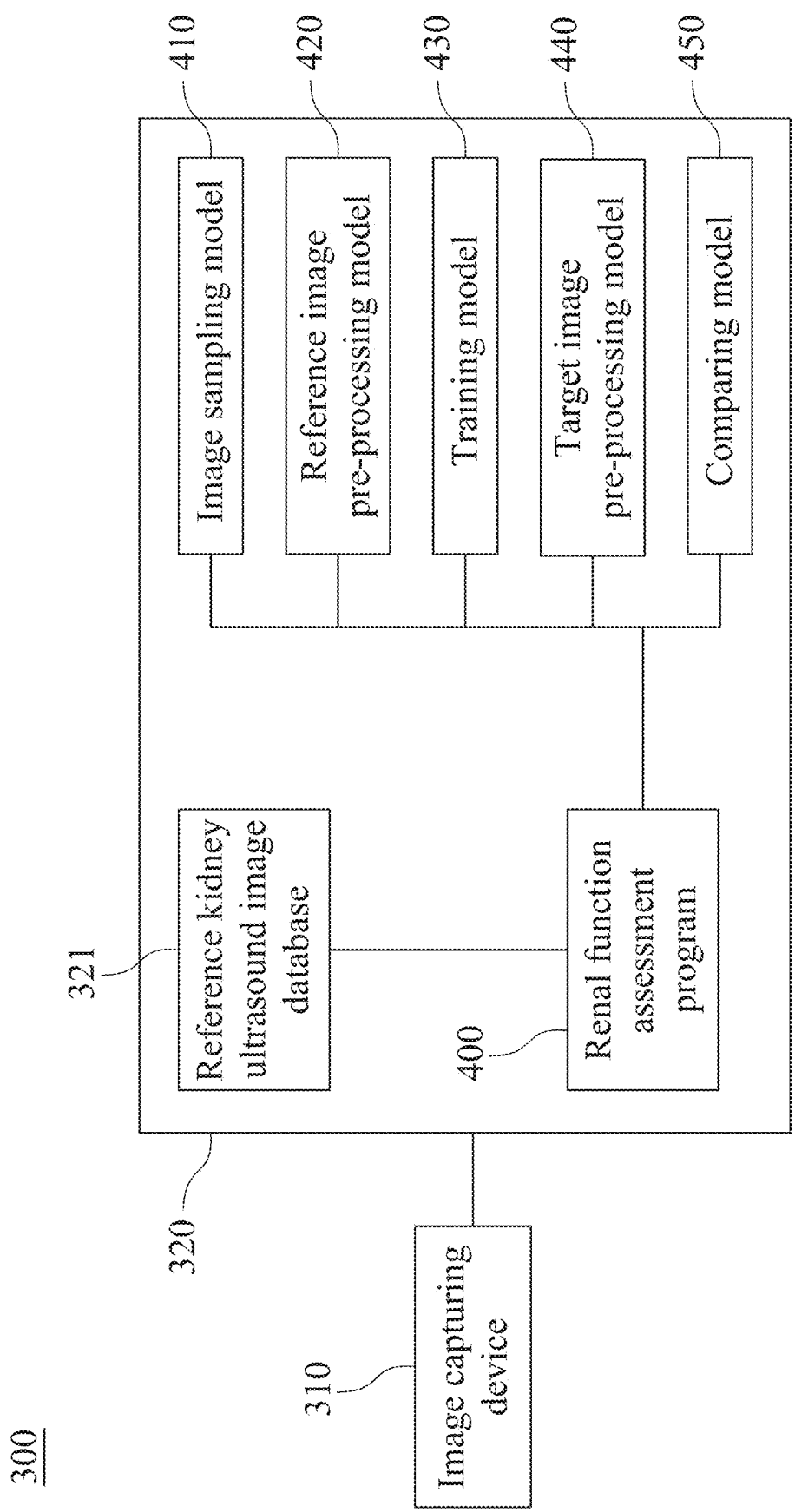
FIG. 4 is a block diagram of a renal function assessment system according to still another embodiment of the present disclosure.

Please refer to FIG. 4, which is a block diagram of a renal function assessment system 300 according to still another embodiment of the present disclosure. The renal function assessment system 300 includes an image capturing device 310 and a processer 320.

The image capturing device 310 is for capturing a target kidney ultrasound image data of a subject. In detail, the target kidney ultrasound image data can be connected to an EMR of the subject, and the EMR can include the information of the gender and the age of the subject, the laboratory test results (such as serum creatinine) or other special treatment procedures, such as medication history, comorbidities, or admission records, so that it is favorable for facilitating the following assessment and comparison.

The processer 320 is electronically connected to the image capturing device 310, wherein the processer 320 includes a reference kidney ultrasound image database 321 and a renal function assessment program 400, and the reference kidney ultrasound image database 321 includes a plurality of reference kidney ultrasound image data (not shown). Each of the reference kidney ultrasound image data can be connected to an EMR of the corresponding reference subject, and the EMR can include the information of the gender and the age of the reference subject, the laboratory test results (such as serum creatinine) or other special treatment procedures, such as medication history, comorbidities, or admission records, to enhance the data integrity of each of the reference kidney ultrasound image data.

As shown in FIG. 4, the renal function assessment program 400 includes an image sampling model 410, a reference image pre-processing model 420, a training model 430, a target image pre-processing model 440 and a comparing model 450.

The image sampling model 410 is for sampling the reference kidney ultrasound image data randomly by an ensemble learning module (not shown) to obtain a testing image dataset (not shown) and a validation image dataset (not shown). In detail, the ensemble learning module can sample the reference kidney ultrasound image data of the reference kidney ultrasound image database 321 centrally and uniformly, and the reference kidney ultrasound image data used to establish the first deep-learning classifier will be replaced randomly during the sampling process thereof, so that the established strength of the first deep-learning classifier can be increased and the assessing accuracy of the renal function assessment program 400 of the present disclosure can be enhanced. In specific, the ensemble learning module can be a bootstrap aggregating classifier, but the present disclosure is not limited thereto.

The reference image pre-processing model 420 is for adjusting an image size of each of the reference kidney ultrasound image data of the testing image dataset, wherein each of the reference kidney ultrasound image data is normalized according to an average and a standard deviation of a visual image database to obtain a plurality of after-processed reference kidney ultrasound image data. In detail, the image size of each of the reference kidney ultrasound image data will be adjusted to 224 pixels×224 pixels based on an area where the kidney is located, and each of the reference kidney ultrasound image data will be normalized according to the average and the standard deviation of Neo4j visual image database, ImageNet visual image database or CIFAR-10 visual image database to facilitate the following analysis.

Furthermore, each of the reference kidney ultrasound image data can be processed by a reference image data reinforcement method in the reference image pre-processing model 420, and the reference image data reinforcement method is a displacement noise reinforcing method, a rolling noise reinforcing method or a horizontal flip noise reinforcing method to increase the amount of information of each of the reference kidney ultrasound image data, so that it is favorable for enhancing the accuracy of the following assessment.

The training model 430 is for achieving a convergence of the after-processed reference kidney ultrasound image data by a deep learning module to obtain a first deep-learning classifier. In detail, the deep learning module can be ResNet-101 calculus module to enhance the assessing accuracy of the renal function assessment system 300 of the present disclosure.

In specific, the conventional ResNet-101 calculus module includes 101 training layers, and the first deep-learning classifier of the present disclosure further replaces the last four training layers of the conventional ResNet-101 calculus module by four consecutive fully connected layers, namely two first fully connected layers, a second fully connected layer and an output layer (about 1000-class classifier), wherein the two first fully connected layers are connected to each other consecutively and further connected to the second fully connected layer, and the second fully connected layer is connected to the output layer consecutively. The image feature of the after-processed target kidney ultrasound image data is output from the second fully connected layer, and the assessing result of eGFR is output from the output layer. In this time, the image feature presents a 256-dimension vector corresponding to the second fully connected layer, the 256-dimension vector will be further trained by the first deep-learning classifier of the present disclosure until a complete convergence is achieved, and then the assessing result of eGFR will be output from the output layer. Therefore, the assessing accuracy of eGFR of the renal function assessment system 300 of the present disclosure can be further enhanced.

The target image pre-processing model 440 is for adjusting an image size of the target kidney ultrasound image data, wherein the target kidney ultrasound image data is normalized according to the average and the standard deviation of the visual image database to obtain an after-processed reference kidney ultrasound image data. In detail, the image size of the target kidney ultrasound image data will be adjusted to 224 pixels×224 pixels based on an area where the kidney is located, and the target kidney ultrasound image data will be normalized according to the average and the standard deviation of one of Neo4j visual image database, ImageNet visual image database or CIFAR-10 visual image database which is used to normalize each of the reference kidney ultrasound image data to ensure the assessing consistency and correctness of the renal function assessment system 300 of the present disclosure.

Furthermore, the target kidney ultrasound image data can be processed by a target image data reinforcement method in the target image pre-processing model 440, and the target image data reinforcement method is a displacement noise reinforcing method, a rolling noise reinforcing method or a horizontal flip noise reinforcing method to increase the amount of information of the target kidney ultrasound image data. Thus, it is favorable for enhancing the accuracy of the following assessment.

The comparing model 450 is for achieving a convergence of the after-processed target kidney ultrasound image data by the first deep-learning classifier to obtain an image feature of the after-processed target kidney ultrasound image data, and the image feature of the after-processed target kidney ultrasound image data is analyzed by the first deep-learning classifier to obtain an assessing result of eGFR.

Therefore, in the renal function assessment system 300 of the present disclosure, the target kidney ultrasound image data which has pre-processed completely is trained to achieve a convergence by the first deep-learning classifier established by the training model 430, and the image feature obtained therefrom is served as a basis to the following analysis and assessment to provide a rapid, accurate and non-invasive renal function assessment system under the premise that the renal function assessment is based on the information implied in the kidney ultrasound image data.

Figure 5:
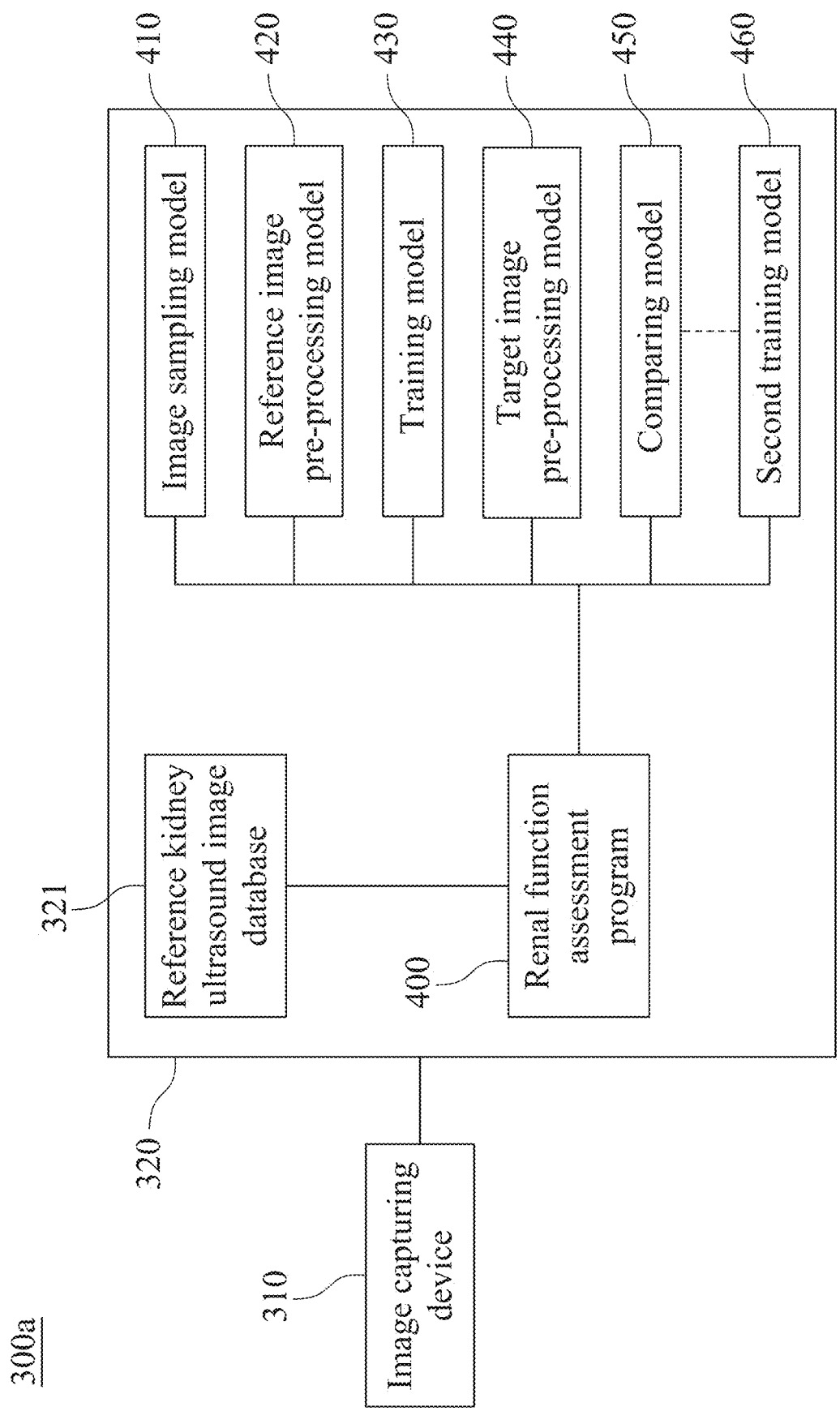
FIG. 5 is a block diagram of a renal function assessment system according to yet another embodiment of the present disclosure.

Please refer to FIG. 5, which is a block diagram of a renal function assessment system 300a according to yet another embodiment of the present disclosure. The renal function assessment system 300a includes an image sampling model 410, a reference image pre-processing model 420, a training model 430, a target image pre-processing model 440, a comparing model 450 and a second training model 460, wherein the image sampling model 410, the reference image pre-processing model 420, the training model 430, the target image pre-processing model 440 and the comparing model 450 of the renal function assessment system 300a are the same with the image sampling model 410, the reference image pre-processing model 420, the training model 430, the target image pre-processing model 440 and the comparing model 450 of the renal function assessment system 300 of FIG. 4, so that the same structural details thereof are not described again therein.

In the second training model 460, a duplicate copy of the image feature of the after-processed target kidney ultrasound image data is trained by a second deep-learning classifier to achieve a convergence and then obtain a second image selected feature weight data, and an assessing status of an advanced CKD, indicting an irreversible kidney failure, is obtained according to the second image selected feature weight data. In specific, the second deep-learning classifier can be XGBoost classifier, but the present disclosure is not limited thereto. In detail, after the image feature is trained by the first deep-learning classifier and achieved a convergence, the image feature has included the eGFR information implied in the target kidney ultrasound image data. In this time, the duplicate copy of the image feature of the after-processed target kidney ultrasound image data will be trained by the second deep-learning classifier to achieve a convergence and then obtain the second image selected feature weight data. Then, the assessing status of the advanced CKD will be obtained according to the critical value of eGFR being 60 ml/min/1.73 m$^2$.

Therefore, by the cooperative training and assessment of the first deep-learning classifier and the second deep-learning classifier, the renal function assessment system 300a of the present disclosure can not only assess the value of eGFR of the subject rapidly and accurately according to the target kidney ultrasound image data thereof, but also further determine whether the subject has an advanced CKD or not. Thus, it is favorable for formulating a medical strategy thereof.

Figure 6:
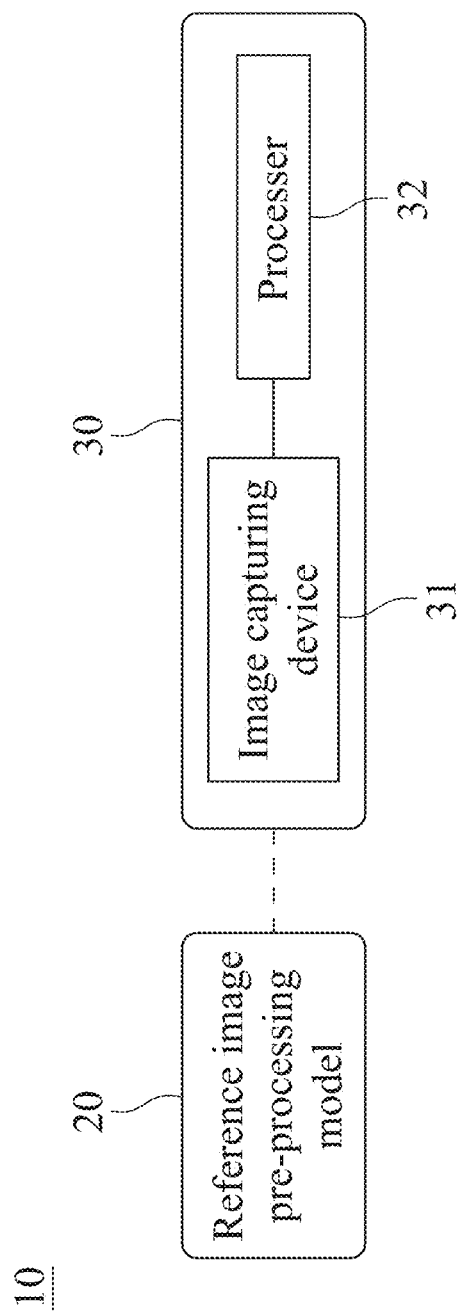
FIG. 6 is a block diagram of a kidney care device according to more another embodiment of the present disclosure.

Please refer to FIG. 6, which is a block diagram of a kidney care device 10 according to more another embodiment of the present disclosure. As shown in FIG. 6, the kidney care device 10 includes a renal function assessment system 30 and an electronic device 20, and the electronic device 20 is electronically connected to the renal function assessment system 30. In detail, the renal function assessment system 30 includes an image capturing device 31 and a processer 32, and the image capturing device 31 and the processer 32 are the similar with that of the renal function assessment system 300 of FIG. 4 or that of renal function assessment system 300a of FIG. 5. The assessing result of eGFR output from the processer 32 or the assessing status of the advance CKD output from the second training model (not shown) of the renal function assessment system 30 will be displayed on the electronic device 20, and the assessing result of the renal function and the following suggestions for medication, referral and other medical policies will be further displayed thereon.

Therefore, by the cooperation of the electronic device and the renal function assessment system of the present disclosure, the medical strategy can be provided according to the assessing result of the renal function of the subject, so that the kidney care device of the present disclosure has application potentials in related fields.

Furthermore, although it is not shown in Figures, in the kidney care device of the present disclosure, the image capturing device can be a palm-sized ultrasound machine to capture the target kidney ultrasound image data of the subject, and the electronic device can be a cell phone, a tablet or other portable electronic devices. Moreover, the processer can be further integrated into the electronic device, so that it is not only convenient to carry, but also favorable for enhancing the sensitivity and convenience of the following large-scale renal function assessment, but the present disclosure is not limited thereto.

Example

I. Reference Database

The reference database used in the present disclosure is the kidney ultrasound image data collected by China Medical University Hospital. This clinical research study is approved by China Medical University & Hospital Research Ethics Committee, which are numbered as CMUH105-REC3-068 and CMUH106-REC3-118. The reference database includes 203,353 of kidney ultrasound image data of 8,281 subjects that are aged from 20 to 89 years old and suffered from chronic kidney disease (CKD), wherein all of the aforementioned subjects suffered from CKD are underwent a blood test of serum creatinine within four weeks before and after the ultrasound examination, and the values of serum creatinine are recorded in the electronic medical records thereof to facilitate the following assessment and comparison.

Next, the aforementioned 203,353 of kidney ultrasound image data are further filtered to select the kidney ultrasound image data which has a high image quality and includes the kidney length data marked by the nephrologist during the ultrasound examination and the data of the serum creatinine level. Then, 4,505 of kidney ultrasound image data obtained from 1,446 of the uniquely identifiable primary sonographic studies of 1,299 subjects suffered from the advanced CKD were finally selected as the reference kidney ultrasound image data of the reference kidney ultrasound image database of the present disclosure to process the following assessment.

II. Image Pre-Process

In the image pre-process, the "findContours" function of the cv2 module in Python programming language is applied to each of the 4,505 reference kidney ultrasound image data to isolate "bean-shaped" kidneys from irrelevant information surrounding the kidneys, such as the supplier's logo, to enhance the image quality of the reference kidney ultrasound image data.

Figure 7:
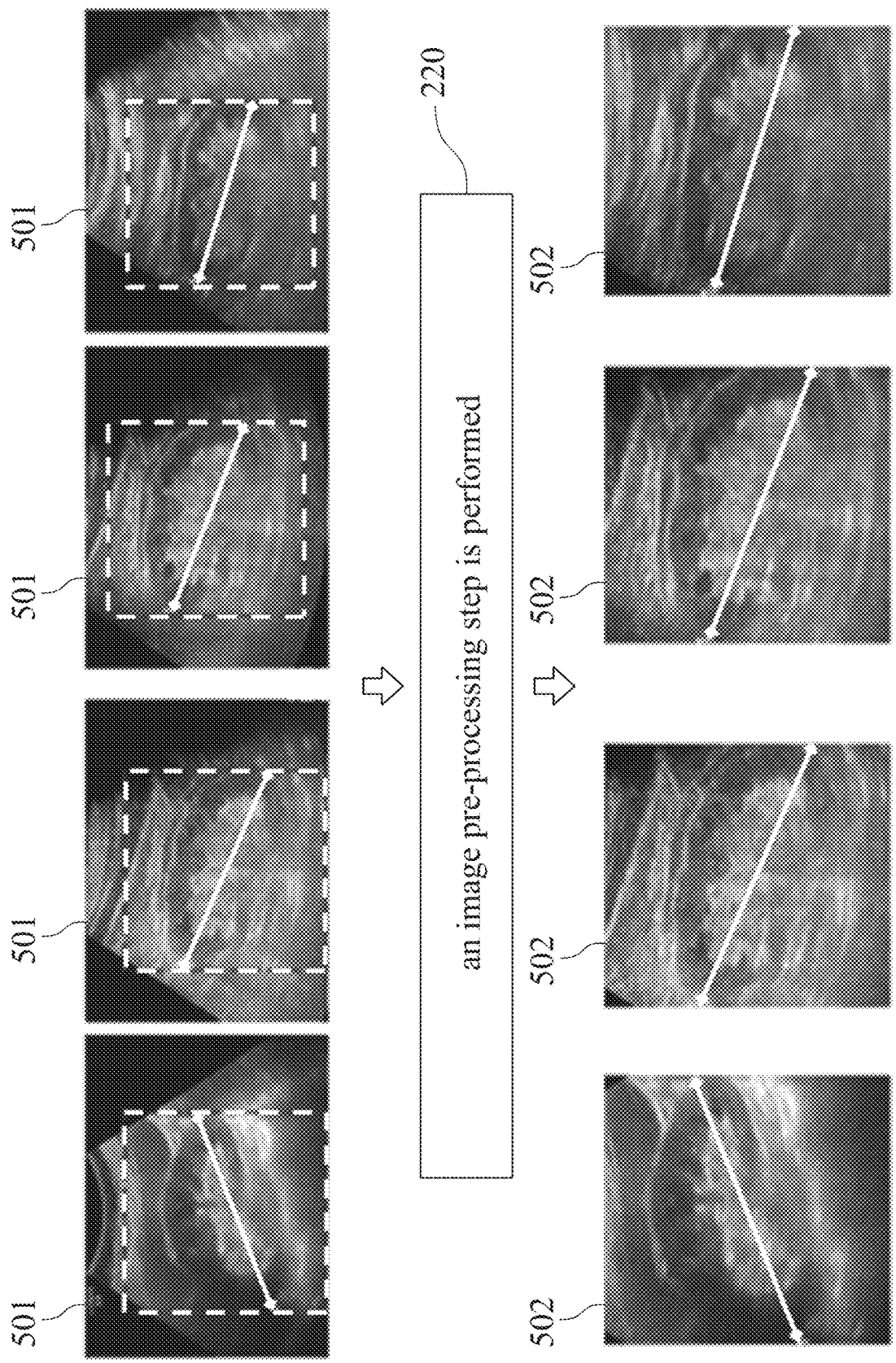
FIG. 7 is a flow chart of an image pre-processing step of the renal function assessment method of the present disclosure.

Please refer to FIG. 7, which is a flow chart of an image pre-processing step of the renal function assessment method of the present disclosure. As shown in FIG. 7, before the plurality of the reference kidney ultrasound image data 501 are used to establish the first deep-learning classifier, each of the reference kidney ultrasound image data 501 is adjusted based on the two markers of the kidney length made by the nephrologist during the ultrasound examination to remove the irrelevant peripheral region of the kidneys. In detail, in Step 220, the reference image pre-processing model will identify the positions of the two markers ($x_1$, $y_1$) and ($x_2$, $y_2$) of the kidney length and then calculate the distance d there-between and the middle point ($x_c$, $y_c$) thereof automatically, and each of the reference kidney ultrasound image data 501 will be adjusted by cropping the square region centered at the middle point ($x_c$, $y_c$) with a length d. Then, an image size of each of the reference kidney ultrasound image data 501 will be adjusted to 224 pixels×224 pixels. After the size adjustment is completely, each of the reference kidney ultrasound image data 501 is processed by a reference image data reinforcement method in the reference image pre-processing model, wherein each of the reference kidney ultrasound image data is processed by a displacement noise reinforcing method, namely shift along x axial or y axial (±10%), a rolling noise reinforcing method (±40 degrees) or a horizontal flip noise reinforcing method, and each of the reference kidney ultrasound image data 501 will be further normalized according to an average and a standard deviation of ImageNet visual image database to obtain a plurality of after-processed reference kidney ultrasound image data 502.

The after-processed reference kidney ultrasound image data 502 processed by Step 220 will be further used to establish the first deep-learning classifier of the present disclosure.

III. The First Deep-Learning Classifier of the Present Disclosure

Figure 8:
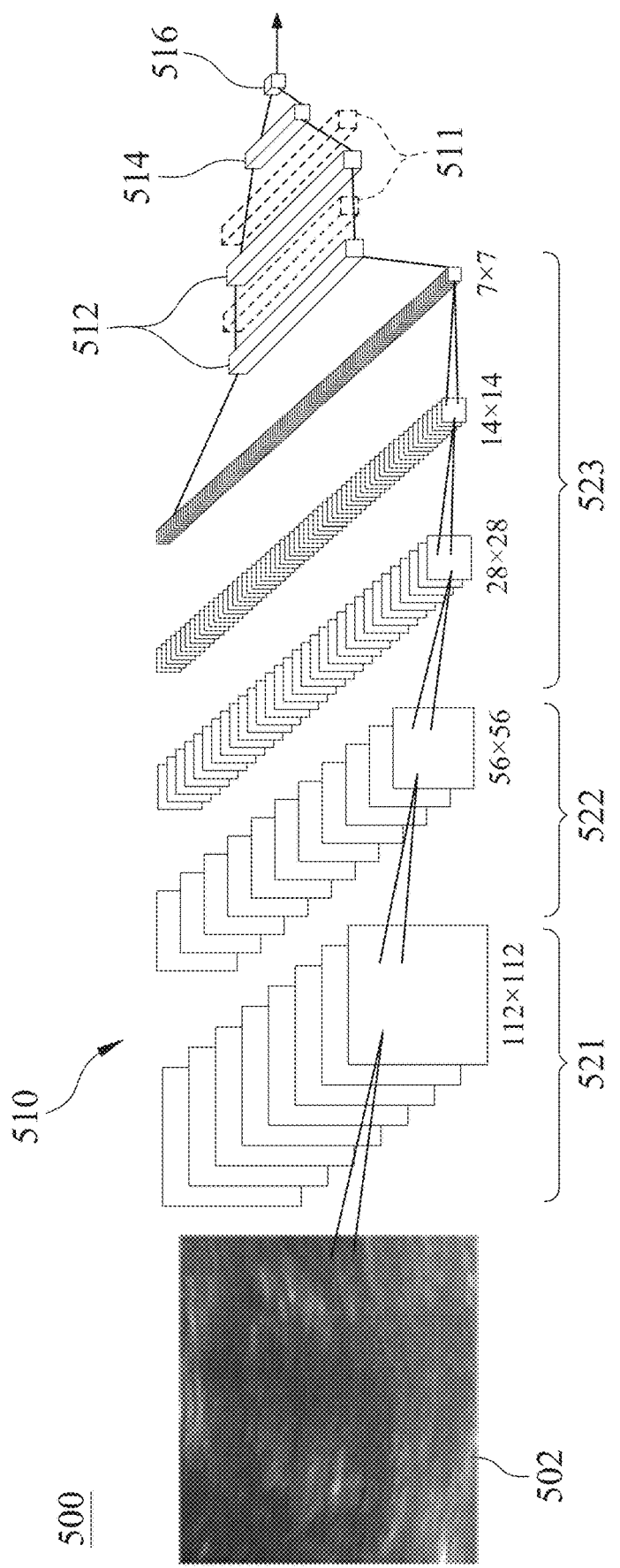
FIG. 8 is a block diagram of a first deep-learning classifier of the present disclosure.

Please refer to FIG. 8, which is a block diagram of a first deep-learning classifier 500 of the present disclosure. The first deep-learning classifier 500 of the present disclosure is a deep learning classifier optimized based on the ResNet-101 calculus module 510.

In detail, in the establishment of the first deep-learning classifier 500 of the present disclosure, first, each of the after-processed reference kidney ultrasound image data 502 will be input to the ResNet-101 calculus module 510 first to be trained until achieving a convergence and then obtain the first deep-learning classifier 500 of the present disclosure, wherein the ResNet-101 calculus module 510 includes a plurality of convolution layers 521, a plurality of MaxPool layers 522 and a plurality of residual blocks 523, which has a total of 101 training layers.

Then, in order to enhance the accuracy of the assessing results of eGFR, in the ResNet-101 calculus module 510 of the present disclosure, the last four layers (about 1000-class classifier) of the conventional ResNet-101 calculus module are further replaced by four consecutive fully connected layers, namely two first fully connected layers 512, a second fully connected layer 514 and an output layer 516, wherein the two first fully connected layers 512 are connected to each other consecutively and further connected to the second fully connected layer 514, and the second fully connected layer 514 is connected to the output layer 516 consecutively. Furthermore, in the example of FIG. 8, the first deep-learning classifier 500 can further include two dropout layers 511, wherein the two dropout layers 511 are disposed respectively between one of the first fully connected layers 512 and the other of the first fully connected layers 512, and between the other of the first fully connected layers 512 and the second fully connected layer 514 to reduce the overfitting between every two consecutive fully connected layers. Furthermore, the output layer 516 can further adopt a linear activation function to calculate the image feature output from the second fully connected layer 514, and a mean-square error (MSE) of the image feature will be optimized by the following Formula (I) to solve a regression-type problem with the output values ranging from 0 to >100.

$$MSE = \frac{1}{n}\sum_{i=1}^{n}(\hat{Y}_i - Y_i); \qquad \text{Formula (I)}$$

wherein $\hat{Y}_i$ and $Y_i$ respectively represent the predicted value of eGFR of the reference kidney ultrasound image data i and the actual value of eGFR of the reference kidney ultrasound image data i.

Next, the after-processed reference kidney ultrasound image data 502 will be trained to achieve a convergence by the ResNet-101 calculus module 510 of the present disclosure to obtain the first deep-learning classifier 500 of the present disclosure for following assessment and analysis.

IV. The Renal Function Assessment System of the Present Disclosure

Figure 9:
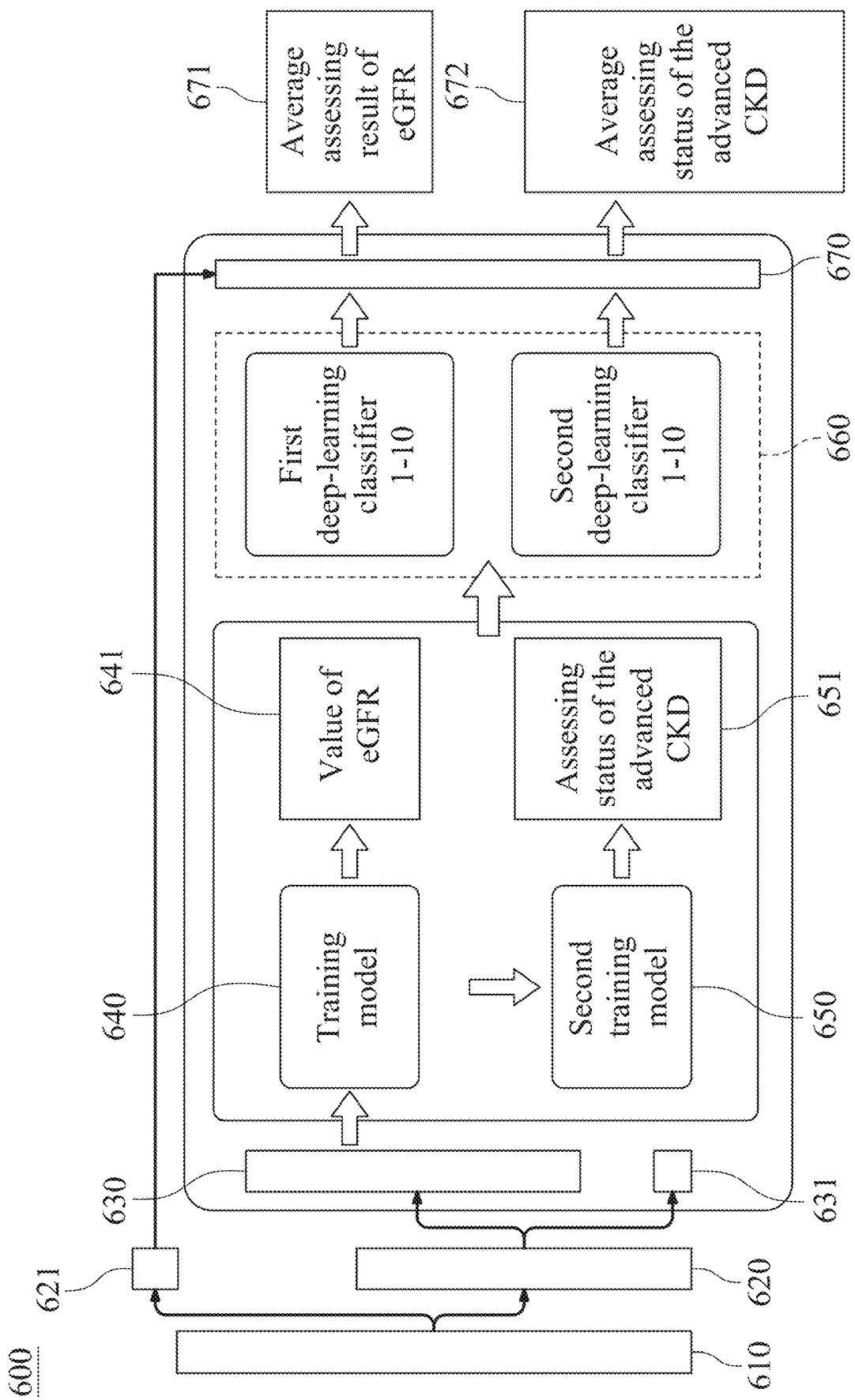
FIG. 9 is an analysis flow chart of the renal function assessment system of the present disclosure.

Please refer to FIG. 9, which is an analysis flow chart of the renal function assessment system 600 of the present disclosure, and the renal function assessment method of the present disclosure and the renal function assessment system 600 of the present disclosure will be further illustrated by FIG. 9.

First, in order to make the training function of the renal function assessment system 600 of the present disclosure have a lower mean absolute error (MAE), as shown in FIG. 9, the 1,446 uniquely identifiable primary sonographic studies of 1,299 subjects suffered from the end-stage renal disease of the reference kidney ultrasound image database 610 are partitioned and grouped based on the unique and hashed patient identification keys to make ensure that the uniquely identifiable primary sonographic studies of the same subject will not be grouped into different groups, and the 1,446 uniquely identifiable primary sonographic studies will be partitioned into a non-testing group 620 and a testing group 621. The non-testing group 620 includes 1,285 uniquely identifiable primary sonographic studies (about 90% of the uniquely identifiable primary sonographic studies of the reference kidney ultrasound image database 610), the testing group 621 includes 161 uniquely identifiable primary sonographic studies (about 10% of the uniquely identifiable primary sonographic studies of the reference kidney ultrasound image database 610), and the reference kidney ultrasound image data of the testing group 621 are further named as "target kidney ultrasound image data" for the following assessment and validation.

Then, the reference kidney ultrasound image data of the non-testing group 620 will be sampled randomly by an ensemble learning module of the image sampling model (not shown) to obtain a testing image dataset 630 and a validation image dataset 631, wherein the aforementioned ensemble learning module is a bootstrap aggregating classifier. The bootstrap aggregating classifier is also known as a bagging classifier and is used to sample the samples of a training set uniformly and sample randomly with replacement to avoid the probability of overfitting during a single sampling process. The aforementioned randomly sampling process is performed 10 times to obtain 10 pairs of the testing image datasets 630 and the validation image datasets 631.

Next, the reference kidney ultrasound image data of the 10 testing image datasets 630 are respectively processed by the reference image pre-processing model to obtain a plurality of after-processed reference kidney ultrasound image data. The after-processed reference kidney ultrasound image data will be trained and then used to establish the first deep-learning classifier of the present disclosure by the training model 640 to output a value of eGFR 641 correspondingly. In detail, the image feature output form the second fully connected layer (not shown) of the first deep-learning classifier is a 256-dimension vector, the 256-dimension vector will be further trained by the first deep-learning classifier, and then the first deep-learning classifier will output the value of eGFR 641. In this time, the duplicate copy of the image feature being a 256-dimension vector will be trained by the XGBoost classifier of the second training model 650 to achieve a convergence and then obtain a second deep-learning classifier of the present disclosure, and a second image selected feature weight data will be obtained. Then, an assessing status of the advanced CKD 651 will be obtained according to the second image selected feature weight data by the second deep-learning classifier of the present disclosure, wherein the assessing status of the advanced CKD 651 is defined by the critical point of eGFR being 60 ml/min/1.73 m², indicating an irreversible kidney failure.

After finishing the aforementioned steps, the 10 testing image datasets 630 are trained, respectively, to obtain 10 first deep-learning classifiers and 10 second deep-learning classifiers, and 10 values of eGFR 641 and 10 assessing status of the advanced CKD 651 are obtained correspondingly. The aforementioned 10 values of eGFR 641 and 10 assessing status of the advanced CKD 651 are further classified, respectively, to obtain average values thereof by a calculating models 660, and an average assessing result of eGFR 671 and an average assessing status of the advanced CKD 672 will be further obtained.

V. The Assessing Efficiency of the Renal Function Assessment System of the Present Disclosure The assessing efficiency of the renal function assessment system of the present disclosure is analyzed by the target kidney ultrasound image data of the testing group 621, wherein the target kidney ultrasound image data of the testing group 621 are respectively analyzed and trained by 10 first deep-learning classifiers and 10 second deep-learning classifiers to analyze the variances between the assessing results of eGFR generated from the renal function assessment system of the present disclosure and the actual values of eGFR, and between the assessing status of the advanced CKD generated from the renal function assessment system of the present disclosure.

In the present analysis, an image size of each of the target kidney ultrasound image data of the testing group 621 will be adjusted to 224 pixels×224 pixels by the target image pre-processing model, and each of the target kidney ultrasound image data will be normalized according to the average and the standard deviation of ImageNet visual image database to obtain a plurality of after-processed target kidney ultrasound image data.

Please refer to FIG. 9 again, after the pre-processing process of the target kidney ultrasound image data is finished, in order to reduce the variance among the 10 first deep-learning classifiers, the aforementioned 10 values of eGFR will be further averaged by the comparing model 670 and then quantified by using mean absolute error method, Pearson's correlation method and Coefficient of determination method (R-squared method), wherein the formulations of mean absolute error method are presented as Formula (II-1) and Formula (II-2), the formulation of Pearson's correlation method is presented as Formula (III), and the formulation of Coefficient of determination method is presented as Formula (IV).

$$\hat{Y}_i = \frac{1}{10}\sum_{j=1}^{10} y_{ij}; \quad \text{Formula (II-1)}$$

$$MAE = \frac{1}{n}\sum_{i=1}^{n}\left|(\hat{Y}_i - Y_i)\right|; \quad \text{Formula (II-2)}$$

wherein $y_{ij}$ represents the value of eGFR of the target kidney ultrasound image data i generated from the first deep-learning classifier j, and $Y_i$ is the actual value of the eGFR of the target kidney ultrasound image data i;

$$\rho_{Y,\hat{Y}} = \frac{\text{cov}(Y, \hat{Y})}{\sigma_Y \cdot \sigma_{\hat{Y}}}; \quad \text{Formula (III)}$$

$$R^2 = 1 - \frac{SS_{res}}{SS_{tot}}; \quad \text{Formula (IV)}$$

wherein $SS_{res}$ is obtained from Formula (IV-i), and $SS_{tot}$ is obtained from Formula (IV-ii).

$$SS_{res} = \sum_{i=1}^{n}(Y_i - \overline{Y_i})^2; \quad \text{Formula (IV-i)}$$

$$SS_{tot} = 1 - \frac{SS_{res}}{SS_{tot}}. \quad \text{Formula (IV-ii)}$$

Please refer to Table 2, which shows the mean absolute error (MAE), the Pearson's correlation and the Coefficient of determination (R-squared) of the aforementioned 10 values of eGFR.

TABLE 2

| MAE | Pearson's correlation | R-squared |
|---|---|---|
| 17.605 | 0.741 | 0.421 |

Furthermore, the aforementioned 10 assessing status of the advanced CKD 651 will be further averaged to obtain the average assessing status of the advanced CKD 672, wherein the dropout probability thereof is set at 0.5, and the calculation formulations thereof are presented as Formula (V-1) and Formula (V-2).

$$\hat{P}_i = \frac{1}{10}\sum_{j=1}^{10} P_{ij}, \quad \text{Formula (V-1)}$$

$$\hat{Y}_i = \begin{cases} 0, \hat{P}_i < 0.5 \\ 1, \hat{P}_i \geq 0.5 \end{cases} ; \quad \text{Formula (V-2)}$$

wherein $P_{ij}$ represents the assessing status of the advanced CKD obtained from the value of eGFR of the target kidney ultrasound image data i which is analyzed by and then generated from the second deep-learning classifier j.

Figure 10:
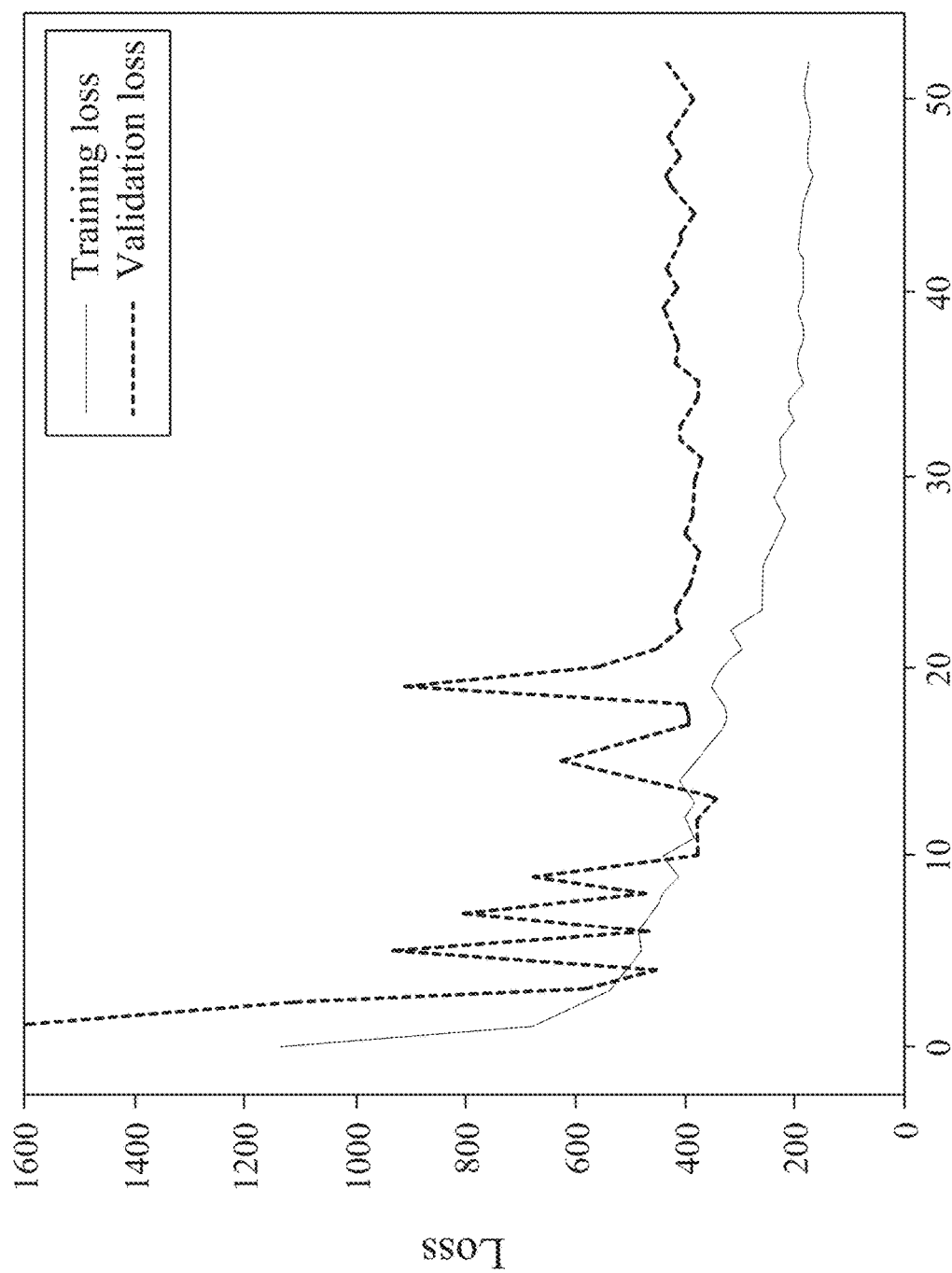
FIG. 10 shows a learning curve of training loss and validation loss of the first deep-learning classifier of the present disclosure.
Figure 11:
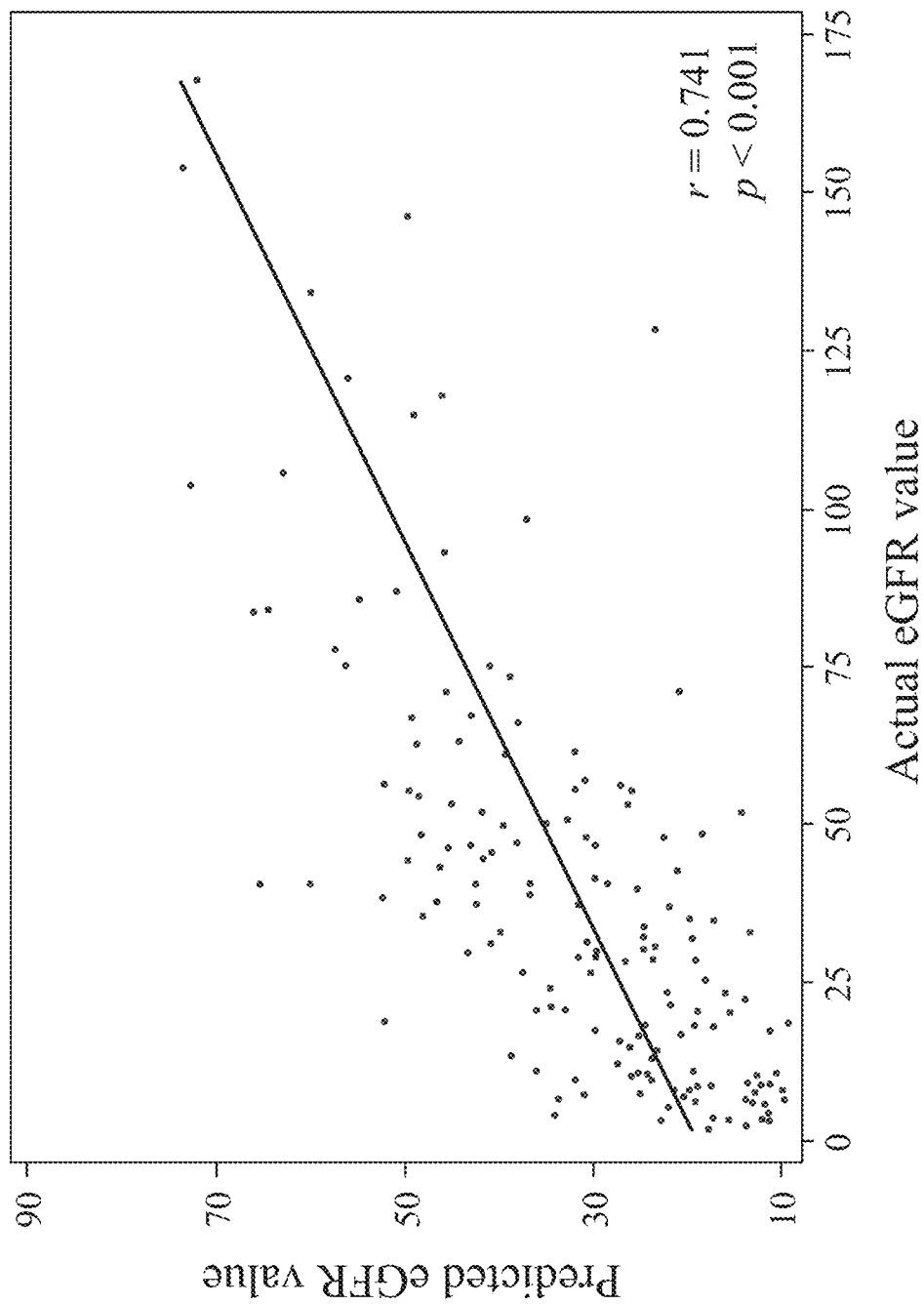
FIG. 11 shows a relationship scatter plot of actual eGFR values and predicted eGFR values of the first deep-learning classifier of the present disclosure.

Please refer to FIG. 10 and FIG. 11, wherein FIG. 10 shows a learning curve of training loss and validation loss of the first deep-learning classifier of the present disclosure, and FIG. 11 shows a relationship scatter plot of actual eGFR values and predicted eGFR values of the first deep-learning classifier of the present disclosure. As shown in FIG. 10, after averaging 10 values of eGFR, the smallest overfitting has occurred when the number of the training epoch is 14, wherein the mean absolute error between the assessing result of eGFR of the testing group 621 and the actual value of eGFR thereof is 0.741, and the mean absolute error there between is 17.605. Therefore, it is shown that the assessing accuracy of eGFR of the renal function assessment system of the present disclosure is excellent. Furthermore, as shown in FIG. 11, the Pearson's correlation between the assessing result of eGFR of the testing group 621 and the actual value of eGFR thereof is up to 0.74, and it is further shown that the assessing accuracy of the renal function assessment system of the present disclosure is exactly excellent.

Figure 12:
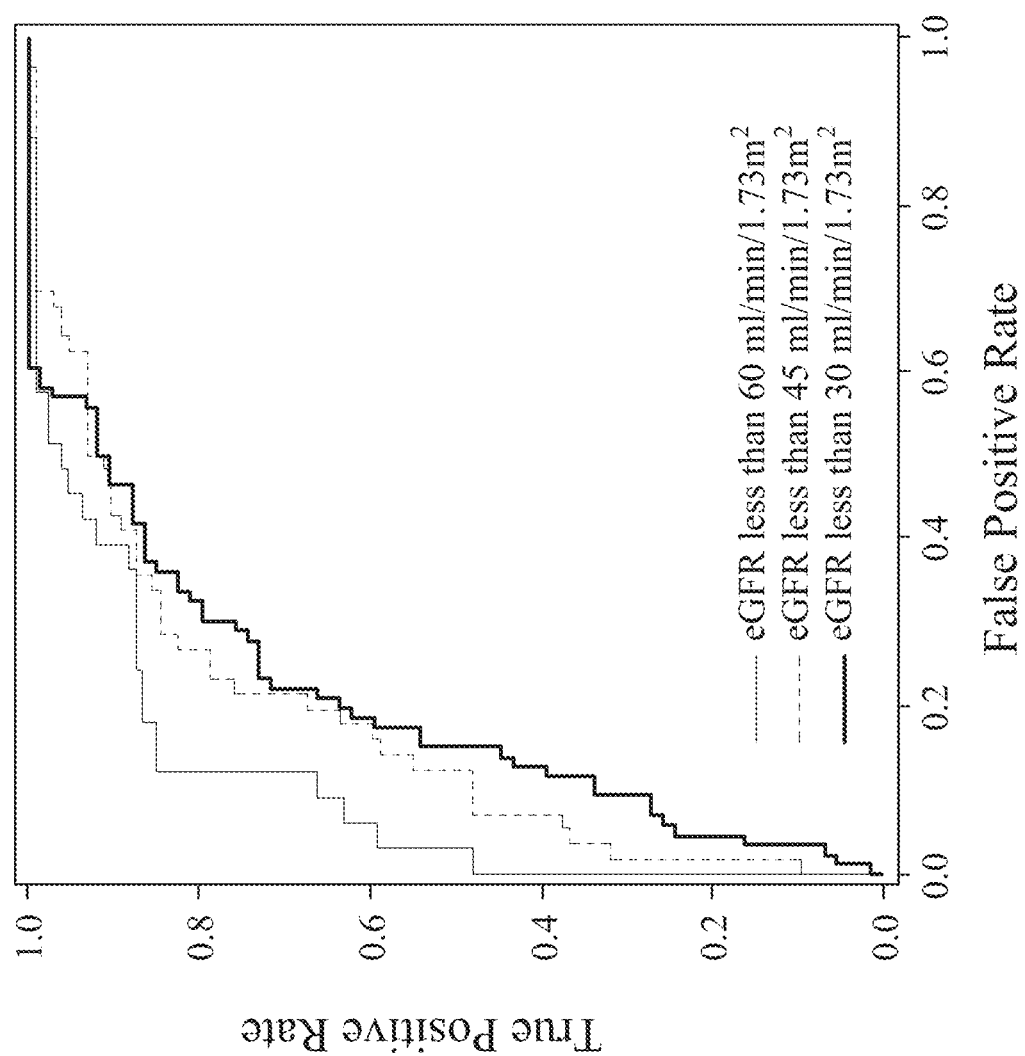
FIG. 12 is a receiver operating characteristic curve (ROC) diagram of the renal function assessment system of the present disclosure.

Please refer to FIG. 12, which is a receiver operating characteristic curve (ROC) diagram of the renal function assessment system of the present disclosure. As shown in FIG. 12, when the renal function assessment system of the present disclosure is used to assess the value of eGFR of the subject and the critical point of eGFR is set at 60 ml/min/1.73 m², the area under the receiver operating characteristic curve (AUROC) thereof can reach to 0.9036, and the assessing accuracy thereof is 85.6%. Furthermore, if the critical point of eGFR is set at 45 ml/min/1.73 m² and 30 ml/min/1.73 m², respectively, the AUROC thereof can also respectively reach to 0.8326 and 0.8036. Therefore, it is shown that the assessing accuracy of eGFR and the status of the advanced CKD of the renal function assessment system of the present disclosure is excellent.

Figure 13:
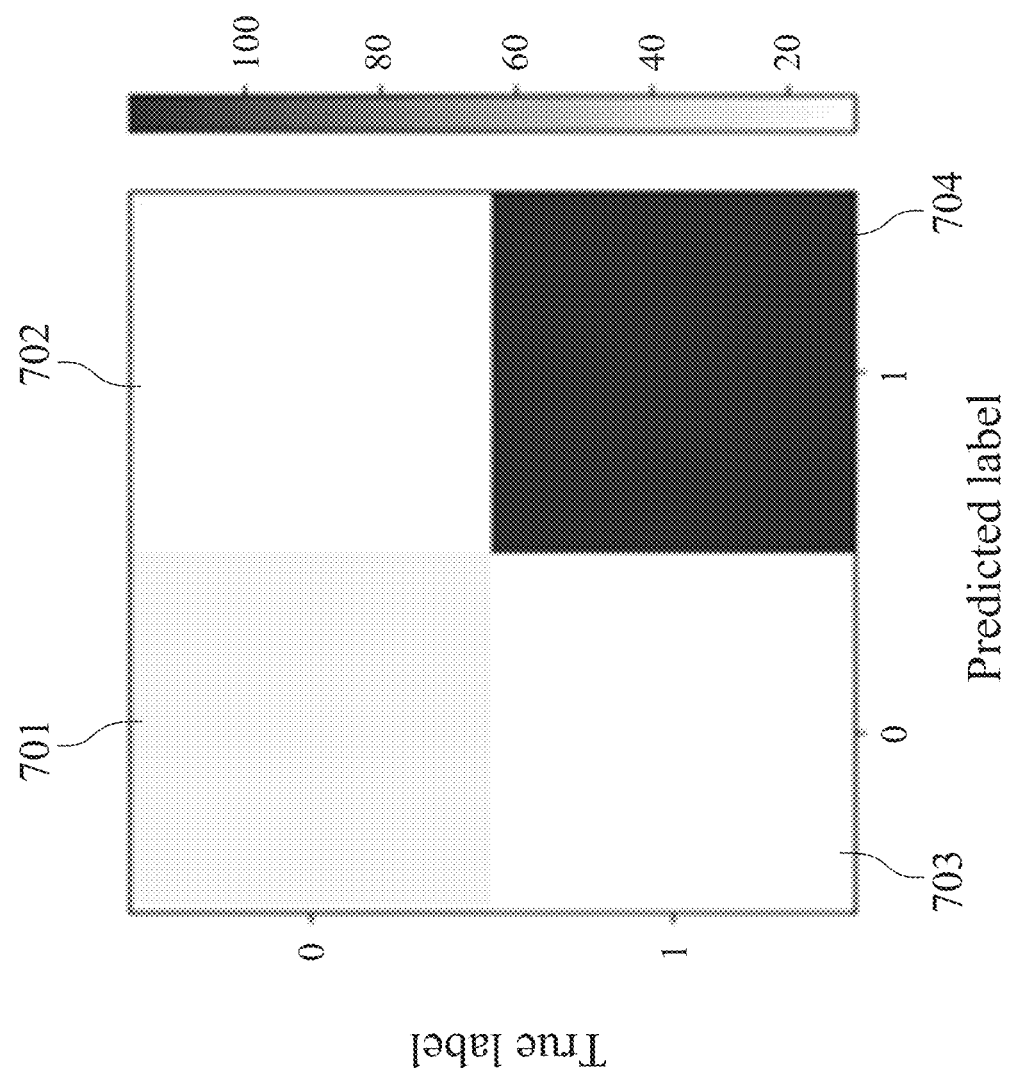
FIG. 13 is a confusion matrix diagram of the renal function assessment system of the present disclosure used to assess a subject's status of an advanced chronic kidney disease.

Please refer to FIG. 13, which is a confusion matrix diagram of the renal function assessment system of the present disclosure used to assess a subject's status of the advanced chronic kidney disease. In FIG. 13, the critical point of eGFR is 60 ml/min/1.73 m² to analyze the accuracy of the assessing status of the advanced CKD, indicating an irreversible kidney failure, of the renal function assessment system of the present disclosure. As shown in FIG. 13, the number of the uniquely identifiable primary sonographic studies falling in the true negative (TN) block 701, which is without the irreversible kidney failure, of the predicted labels is 20, the number of the uniquely identifiable primary sonographic studies falling in the false positive (FP) block 702, which is with the irreversible kidney failure, of the predicted labels is 13, the number of the uniquely identifiable primary sonographic studies falling in the false negative (FN) block 703, which is without the irreversible kidney failure, of the predicted labels is 10, and the number of the uniquely identifiable primary sonographic studies falling in the true positive (TP) block 704, which is with the irreversible kidney failure, of the predicted labels is 117.

Please refer to FIG. 12, FIG. 13 and Table 3 simultaneously, wherein Table 3 shows the assessing results of the renal function assessment system of the present disclosure used to assess the value of eGFR and the status of the advanced CKD of the subjects.

TABLE 3

| Critical value of eGFR (ml/min/1.73 m²) | 30 | 45 | 60 |
|---|---|---|---|
| Value of confusion matrix | TN = 66  FP = 20 FN = 21  TP = 53 | TN = 41  FP = 15 FN = 20  TP = 84 | TN = 20  FP = 13 FN = 10  TP = 117 |
| Accuracy | 74.38 | 78.13 | 85.63 |
| AUROC | 0.8036 | 0.8326 | 0.9036 |
| Sensitivity | 0.7027 | 0.8077 | 0.9213 |
| Specificity | 0.7791 | 0.7321 | 0.6061 |

As shown in the aforementioned results, the accuracy, the sensitivity and the specificity of the renal function assessment system of the present disclosure used to assess the eGFR and the status of the advanced CKD of the subjects are excellent. Thus, the renal function assessment system, the renal function assessment method and the kidney care device of the present disclosure can accurately assess the renal function of the subjects based on the target kidney ultrasound image data thereof and can provide a rapid, accurate and non-invasive renal function assessment system. Accordingly, it is favorable for avoiding the assessing error in the conventional renal function assessment method caused by different subjective interpretation habits of different analysts.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A renal function assessment method, comprising:
providing a target kidney ultrasound image data of a subject;
performing an image pre-processing step by a target image pre-processing model, wherein an image size of the target kidney ultrasound image data is adjusted, and the target kidney ultrasound image data is normalized according to an average and a standard deviation of a visual image database to obtain an after-processed target kidney ultrasound image data;
performing a feature extracting step by a first deep-learning classifier, wherein the after-processed target kidney ultrasound image data is trained to achieve a convergence by the first deep-learning classifier to obtain an image feature of the after-processed target kidney ultrasound image data; and
performing a determining step by the first deep-learning classifier, wherein the image feature of the after-processed target kidney ultrasound image data is analyzed by the first deep-learning classifier to obtain an assessing result of an estimated glomerular filtration rate (eGFR).

2. The renal function assessment method of claim 1, wherein the target kidney ultrasound image data is further processed by an image data reinforcement method in the image pre-processing step.

3. The renal function assessment method of claim 2, wherein the target kidney ultrasound image data is processed by a displacement noise reinforcing method, a rolling noise reinforcing method or a horizontal flip noise reinforcing method in the image data reinforcement method.

4. The renal function assessment method of claim 1, wherein the first deep-learning classifier comprises two first fully connected layers, a second fully connected layer and an output layer, the two first fully connected layers are connected to each other consecutively and further connected to the second fully connected layer, and the second fully connected layer is connected to the output layer consecutively;
wherein the image feature of the after-processed target kidney ultrasound image data is output from the second fully connected layer, and the assessing result of the eGFR is output from the output layer.

5. The renal function assessment method of claim 1, further comprising:
performing a module establishing step by a renal function assessment program to obtain the first deep-learning classifier, wherein the module establishing step comprises:
providing a reference kidney ultrasound image database, wherein the reference kidney ultrasound image database comprises a plurality of reference kidney ultrasound image data;
performing a pre-training image processing step by a reference image pre-processing model of the renal function assessment program, wherein an image size of each of the reference kidney ultrasound image data is adjusted, and each of the reference kidney ultrasound image data is normalized according to the average and the standard deviation of the visual image database to obtain a plurality of after-processed reference kidney ultrasound image data; and
performing a training step by a training model of the renal function assessment program, wherein the training step is for achieving a convergence of the after-processed reference kidney ultrasound image data by a deep learning module to obtain the first deep-learning classifier.

6. The renal function assessment method of claim 5, wherein the deep learning module is ResNet-101 calculus module.

7. The renal function assessment method of claim 5, wherein each of the reference kidney ultrasound image data is further processed by a reference image data reinforcement method in the pre-training image processing step, and the reference image data reinforcement method is a displacement noise reinforcing method, a rolling noise reinforcing method or a horizontal flip noise reinforcing method in the reference image data reinforcement method.

8. The renal function assessment method of claim 1, further comprising;
performing a second training step by a second training model, wherein a duplicate copy of the image feature of the after-processed target kidney ultrasound image data is trained by a second deep-learning classifier to achieve a convergence and then obtain a second image selected feature weight data, and an assessing status of an advanced chronic kidney disease (CKD) is obtained according to the second image selected feature weight data;
wherein the assessing status of the advanced CKD indicates an irreversible kidney failure.

9. The renal function assessment method of claim 8, wherein the second deep-learning classifier is XGBoost classifier.

10. A renal function assessment system, comprising:
an image capturing device for capturing a target kidney ultrasound image data of a subject; and
a processor electronically connected to the image capturing device, wherein the processer comprises a reference kidney ultrasound image database and a renal function assessment program, and the reference kidney ultrasound database comprises a plurality of reference kidney ultrasound image data;
wherein the renal function assessment program comprises:
an image sampling model for sampling the reference kidney ultrasound image data randomly by an ensemble learning module to obtain a testing image dataset and a validation image dataset;
a reference image pre-processing model for adjusting an image size of each of the reference kidney ultrasound image data of the testing image dataset, wherein each of the reference kidney ultrasound image data is normalized according to an average and a standard deviation of a visual image database to obtain a plurality of after-processed reference kidney ultrasound image data;
a training model for achieving a convergence of the after-processed reference kidney ultrasound image data by a deep learning module to obtain a first deep-learning classifier;
a target image pre-processing model for adjusting an image size of the target kidney ultrasound image data, wherein the target kidney ultrasound image data is normalized according to the average and the standard deviation of the visual image database to obtain an after-processed reference kidney ultrasound image data; and
a comparing model for achieving a convergence of the after-processed target kidney ultrasound image data by the first deep-learning classifier to obtain an image feature of the after-processed target kidney ultrasound image data, wherein the image feature of the after-processed target kidney ultrasound image data is analyzed by the first deep-learning classifier to obtain an assessing result of an estimated glomerular filtration rate (eGFR).

11. The renal function assessment system of claim 10, wherein the ensemble learning model is a bootstrap aggregating classifier.

12. The renal function assessment system of claim 10, wherein each of the reference kidney ultrasound image data is processed by a reference image data reinforcement method in the reference image pre-processing model, and the target kidney ultrasound image data is processed by a target image data reinforcement method in the target image pre-processing model.

13. The renal function assessment system of claim 12, wherein the reference image data reinforcement method is a displacement noise reinforcing method, a rolling noise reinforcing method or a horizontal flip noise reinforcing method, and the target image data reinforcement method is a displacement noise reinforcing method, a rolling noise reinforcing method or a horizontal flip noise reinforcing method.

14. The renal function assessment system of claim 10, wherein the first deep-learning classifier comprises two first fully connected layers, a second fully connected layer and an output layer, the two first fully connected layers are connected to each other consecutively and further connected to the second fully connected layer, and the second fully connected layer is connected to the output layer consecutively;

wherein the image feature of the after-processed target kidney ultrasound image data is output from the second fully connected layer, and the assessing result of the eGFR is output from the output layer.

15. The renal function assessment system of claim 10, wherein the deep learning module is ResNet-101 calculus module.

16. The renal function assessment system of claim 10, wherein the renal function assessment program further comprises:

a second training model, wherein a duplicate copy of the image feature of the after-processed target kidney ultrasound image data is trained by a second deep-learning classifier to achieve a convergence and then obtain a second image selected feature weight data, and an assessing status of an advanced chronic kidney disease (CKD) is obtained according to the second image selected feature weight data;

wherein the assessing status of the advanced CKD indicates an irreversible kidney failure.

17. The renal function assessment system of claim 16, wherein the second deep-learning classifier is XGBoost classifier.

18. A kidney care device, comprising:

the renal function assessment system of claim 10; and an electronic device electronically connected to the renal function assessment system.

\* \* \* \* \*